(12) United States Patent
Fuller et al.

(10) Patent No.: US 12,193,763 B2
(45) Date of Patent: Jan. 14, 2025

(54) ELECTROMAGNETIC SENSING FOR USE WITH ABLATION TREATMENT

(71) Applicants: S4 Medical Corp, Chagrin Falls, OH (US); Ohio State Innovation Fundation, Columbus, OH (US)

(72) Inventors: William Fuller, Chagrin Falls, OH (US); Emile Daoud, Columbus, OH (US)

(73) Assignees: S4 Medical Corp, Chagrin Falls, OH (US); Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/365,585

(22) Filed: Aug. 4, 2023

(65) Prior Publication Data

US 2023/0380911 A1 Nov. 30, 2023

Related U.S. Application Data

(62) Division of application No. 17/400,443, filed on Aug. 12, 2021.

(Continued)

(51) Int. Cl.
*A61B 34/20* (2016.01)
*A61B 18/14* (2006.01)
*A61B 18/00* (2006.01)

(52) U.S. Cl.
CPC .......... *A61B 34/20* (2016.02); *A61B 18/1492* (2013.01); *A61B 2018/00351* (2013.01);
(Continued)

(58) Field of Classification Search
CPC ................ A61B 34/20; A61B 18/1492; A61B 2018/00351; A61B 2018/00404; A61B 2018/00577; A61B 2018/00702; A61B 2018/00791; A61B 2034/2051; A61B 2018/00291; A61B 2018/00666;
(Continued)

(56) References Cited

U.S. PATENT DOCUMENTS 5,170,803 A 12/1992 Hewson et al.
6,167,297 A * 12/2000 Benaron ................ A61B 5/418
977/869

(Continued)

FOREIGN PATENT DOCUMENTS

EP 4135823 2/2023
WO WO 2017/049313 3/2017
(Continued)

*Primary Examiner* — Sanjay Cattungal
(74) *Attorney, Agent, or Firm* — Levine Bagade Han LLP (57) ABSTRACT

Electromagnetic sensing for use with ablation treatment devices are described. Generally, an elongate body may be configured for introduction into an esophageal lumen and a distal portion may be pivotably coupled to the elongate body such that actuation of the distal portion reconfigures the distal portion within a plane relative to the elongate body. The elongate body may define one or more openings along the distal portion and which are in fluid communication with a fluid port. A sensor may also be positioned near or at a distal end of the distal portion where the sensor is configured to communicate with an electromagnetic navigational system to determine a distance to an ablation catheter.

8 Claims, 8 Drawing Sheets

Related U.S. Application Data (60) Provisional application No. 63/107,968, filed on Oct. 30, 2020.

(52) U.S. Cl.
CPC ............... *A61B 2018/00404* (2013.01); *A61B 2018/00577* (2013.01); *A61B 2018/00702* (2013.01); *A61B 2018/00791* (2013.01); *A61B 2034/2051* (2016.02)

(58) Field of Classification Search
CPC .............. A61B 2090/061; A61B 90/04; A61B 2090/0427; A61M 2025/0166; A61M 25/0127; A61M 25/0136; A61M 25/007; A61M 25/0147
See application file for complete search history.

(56) References Cited

U.S. PATENT DOCUMENTS

| | | | | |
|---|---|---|---|---|
| 6,463,317 | B1* | 10/2002 | Kucharczyk | A61B 17/12136 606/194 |
| 6,493,575 | B1* | 12/2002 | Kesten | A61B 6/12 600/431 |
| 6,675,037 | B1* | 1/2004 | Tsekos | A61B 5/708 600/419 |
| 6,711,429 | B1* | 3/2004 | Gilboa | A61B 5/06 600/407 |
| 6,748,259 | B1* | 6/2004 | Benaron | A61B 5/0084 600/478 |
| 7,604,601 | B2* | 10/2009 | Altmann | A61B 8/4483 600/463 |
| 10,555,776 | B2* | 2/2020 | Govari | G01R 33/4804 |
| 10,646,197 | B2* | 5/2020 | Govari | A61B 8/12 |
| 2006/0106375 | A1 | 5/2006 | Werneth et al. | |
| 2007/0106287 | A1* | 5/2007 | O'Sullivan | A61B 18/1492 607/9 |
| 2007/0135803 | A1 | 6/2007 | Belson | |
| 2008/0033415 | A1* | 2/2008 | Rieker | A61M 25/0147 606/191 |
| 2010/0041949 | A1 | 2/2010 | Tolkowsky | |
| 2016/0351292 | A1 | 12/2016 | Toth et al. | |
| 2018/0168552 | A1* | 6/2018 | Shi | A61B 18/1477 |
| 2018/0310989 | A1 | 11/2018 | McGuckin, Jr. | |
| 2019/0125210 | A1 | 5/2019 | Govari et al. | |
| 2019/0150753 | A1 | 5/2019 | Tiano | |
| 2019/0269834 | A1 | 9/2019 | Oza et al. | |
| 2022/0133413 | A1 | 5/2022 | Fuller et al. | |

FOREIGN PATENT DOCUMENTS

| | | |
|---|---|---|
| WO | WO 2019/174708 | 9/2019 |
| WO | WO 2020/173814 | 9/2020 |
| WO | WO 2022/093359 | 5/2022 |

* cited by examiner

ELECTROMAGNETIC SENSING FOR USE WITH ABLATION TREATMENT

CROSS-REFERENCE TO RELATED APPLICATIONS

This application is a divisional of U.S. patent application Ser. No. 17/400,443 filed Aug. 12, 2021, which claims the benefit of priority to U.S. Prov. 63/107,968 filed Oct. 30, 2020, which his incorporated herein by reference in its entirety.

FIELD OF THE INVENTION

The present invention relates generally to treatment devices having sensing capabilities. In particular, the present invention is related to instruments which can be tracked via electromagnetic sensing mechanisms.

BACKGROUND OF THE INVENTION

Atrial fibrillation affects more than 33 million people worldwide with millions each year being diagnosed. A common treatment option for atrial fibrillation is catheter ablation where a physician uses various modalities of energy delivered from a catheter to ablate cells within the heart intended to restore normal heart rhythm.

When performing catheter ablation, collateral damage can occur to adjacent organs and cells not intended for ablation. Catheter ablation for atrial fibrillation and other arrhythmias occurs inside the left atrium and other regions of the heart or vascular system. The posterior wall of the left atrium and other regions of the heart or vascular system may be in close vicinity and often in direct contract with the esophagus. When ablating the posterior wall of the left atrium or other regions of the heart or vascular system it is not uncommon for energy to pass beyond the heart wall or the vascular system and reach the esophagus and cause thermal damage to the esophageal cells.

Physicians performing catheter ablation on patients with atrial fibrillation or other arrhythmias use a variety of diagnostic and ablation catheters to diagnose, map, and ablate areas inside the heart. These catheters can be tracked using current electromagnetic (EM) systems. In simple terms, these EM systems comprise an electromagnetic field generator (to create the sensing field), sensors that can be picked up within the field, fiducial markers to create reference points, and software that communicates the locations of the sensors. The sensors are placed on the catheters thereby providing location information to the physician.

A rare, but potentially deadly complication of catheter ablation is thermal injury from the ablation energy radiating out and causing injury to the esophagus. Physicians try to mitigate the issue through monitoring of the temperature inside the esophagus, or with use of devices designed to deviate the esophagus. Some deflection devices that utilize suction along with deflection have shown promise.

Accordingly, there is a need for a system which would enable the user to safely move the esophagus as well as know its location in relation to the ablation catheter in order to safely perform catheter ablation, for example within the left atrium or other regions of the heart or vascular system.

BRIEF SUMMARY OF THE INVENTION

Devices and methods are described for the prevention of thermal damage to the esophagus during an ablation treatment, e.g., within the heart or vascular system. Generally, communication between an ablation catheter inside the left atrium or other regions of the heart or vascular system and an esophageal instrument may provide an indication that ablation energy from the ablation catheter may be too close to the esophageal tissue.

A first instrument such as an endoscopic instrument may be configured to provide for detection of its location within the body and a second instrument such as an ablation catheter may also be configured to provide for detection of its location within the body. An ablation catheter may be advanced intravascularly inside the left atrium or other regions of the heart or vascular system, and the endoscopic device may be advanced per-orally inside the esophagus of the patient and into proximity of the ablation catheter. A navigation software system may be used to determine the locations of each device relative to one another and provide this information to the user.

One example of a navigation and mapping system which may be used with the systems described here may include a three-dimensional system such as but not limited to CARTO® System (Biosense Webster, Inc., Irvine, CA) which can be used to provide the user with real-time information of the location of instruments within the body, such as the heart or vascular system. The CARTO® System utilizes an electromagnetic field generated outside of the patient body that communicates with one or more sensors typically placed near the tip of the device which is inserted into the patient body. The sensors communicate their location within the electromagnetic field and the software displays their location often within an anatomical computer rendering of the organ.

One example of an instrument may incorporate a sensor into an endoscopic instrument having an elongate body which is advanceable into the patient body per-orally through the mouth or through the nose and at least partially into the esophagus. A handle assembly may incorporate an actuator such as a knob or lever which may be articulated by the user to reconfigure a distal portion of the body in a number of different configurations. The handle assembly may also incorporate at least one port through which a lumen may extend through the handle assembly and through the body to fluidly communicate with one or more openings defined along the distal portion. The elongate body may be further comprised of a sheath which extends over an underlying structure attached to the handle assembly and which provides structural support to the body such that the body may be advanced into the and through the esophagus or other body lumen.

The sensor positioned near or at the distal end of the elongate body may incorporate at least a single sensor although any number of additional sensors may be incorporated along the body. A second instrument, e.g., ablation catheter, which may be used in a corresponding manner with the instrument may also incorporate at least a single sensor near or at its distal tip. Any number of additional instruments may also be used in combination with instrument and each additional instrument may incorporate at least a single sensor as well to be used in a corresponding manner with the instrument.

During use, the elongate body may be advanced per-orally into the esophagus such that the distal member is positioned within the esophagus adjacent to the left atrium, or other regions of the heart or vascular system of the patient. The suction force may be optionally actuated such that the esophageal tissue surrounding the distal and proximal openings may be adhered to the outer surface of the distal portion of the elongate body.

The relative distance between the tip of the ablation catheter and sensor located on the elongate body may be determined and monitored by the controller prior to and/or during an ablation treatment. With a threshold distance between the ablation catheter and sensor predetermined, e.g., 5 mm to 10 mm, or any selected distance as determined by the user, the ablation catheter may be used to deliver ablation energy for tissue treatment. In the event that the ablation catheter and sensor are moved too close to one another within the threshold distance, an indication may be provided by a controller to the user that the ablation catheter may be too close to the esophageal tissue such that the ablation energy from within the left atrium or other regions of the heart or vascular system may be conducted through the tissue and inadvertently damage the adjacent esophageal tissue.

In the event that the ablation catheter and esophageal tissue are determined to be too close to one another, the controller may be programmed to provide the alert to the user and/or optionally automatically stop the ablation catheter to prevent any esophageal tissue damage. The user may also actuate the knob or lever on the handle assembly to reconfigure the distal portion to rotate in order to reposition a portion of the esophagus away from the exterior of the heart or vascular system such that a larger gap is formed between the two. The distal portion may be actuated while the surrounding esophageal tissue is adhered to the outer surface of the elongate body via a suction force or with the suction force turned off although having the esophageal tissue adhered to the distal portion when deflected can help ensure that the gap is formed between the esophagus and heart tissue or vascular system.

While the distal portion may be actuated manually by the user, the distal portion in other variations may be actuated automatically by the controller upon detecting that the ablation catheter and elongate body are too close to one another. In yet another variation, other sensors such as a temperature sensor may be optionally incorporated along the elongate body and used to monitor for a temperature rise due to the ablation energy from the ablation catheter. If the monitored temperature detected by the temperature sensor rises above a predetermined threshold limit, the controller may provide an indication or alert to the user. Additionally and/or alternatively, the controller may also be programmed to either stop the ablation energy, actuate the distal portion to deflect the esophageal tissue away, or both.

Generally, one variation of a tissue treatment apparatus may generally comprise an elongate body configured for introduction into an esophageal lumen and a handle assembly coupled to the elongate body and having a fluid port in communication with a lumen defined through the elongate body. A distal portion may be pivotably coupled to the elongate body such that actuation of the distal portion reconfigures the distal portion within a plane relative to the elongate body, wherein the elongate body defines one or more openings along the distal portion and which are in fluid communication with the fluid port. A sensor may also be positioned near or at a distal end of the distal portion, wherein the sensor is configured to communicate with an electromagnetic navigational system.

One example of a method of treating a tissue region within a heart or vascular system of a patient body may generally comprise positioning an elongate body having a first sensor positioned near or at a distal end of a distal portion within an esophageal lumen in proximity to the heart or vascular system of the patient body and positioning an ablation catheter having a second sensor positioned near or at a distal end of the ablation catheter within a left atrium or other regions of the heart or vascular system in proximity to the esophageal lumen. A distance between the first sensor within the esophageal lumen relative and the second sensor may also be monitored within the left atrium or other regions of the heart or vascular system and the ablation catheter may be actuated to deliver ablation energy to a tissue surface within the left atrium or other regions of the heart or vascular system while monitoring the position. Additionally, the distal portion of the elongate body may be reconfigured to deflect a region of the esophageal lumen away from the left atrium or other regions of the heart or vascular system when the distance is below a threshold distance.

DETAILED DESCRIPTION OF THE INVENTION

A first instrument such as an endoscopic device may be configured to provide for detection of its location within the body and a second instrument such as an ablation catheter may also be configured to provide for detection of its location within the body. For instance, an ablation catheter may be advanced intravascularly inside the left atrium or other regions of the heart or vascular system such as the pulmonary vessels, then the endoscopic device may be advanced per orally inside the esophagus of the patient and into proximity of the ablation catheter. A navigation software system could be used to determine the locations of each device relative to one another and may provide this information to the user such as a physician. In one variation, the user may want the ablation catheter to be a certain distance away from the endoscopic device positioned within the esophagus. In the event that the two instruments are located too close to one another within a desirable threshold, the system may provide an indication such as an alert or warning that the two instruments are located too close to one another. In the event that the ablation catheter is used to deliver energy to the tissues within the left atrium, the system may also provide an alert or warning to the user prior to delivering the energy if the two instruments are within a specified distance to one another.

One example of a navigation and mapping system which may be used with the systems described here may include a three-dimensional system such as CARTO® System (Biosense Webster, Inc., Irvine, CA) which can be used to provide the user with real-time information of the location of instruments within the body, such as the heart or the vascular system. The CARTO® System utilizes an electromagnetic field generated outside of the patient body that communicate with one or more sensors typically placed near the tip of the device which is inserted into the patient body. The sensors communicate their location within the electromagnetic field and the software displays their location often within an anatomical rendering of the organ.

Figure 1:
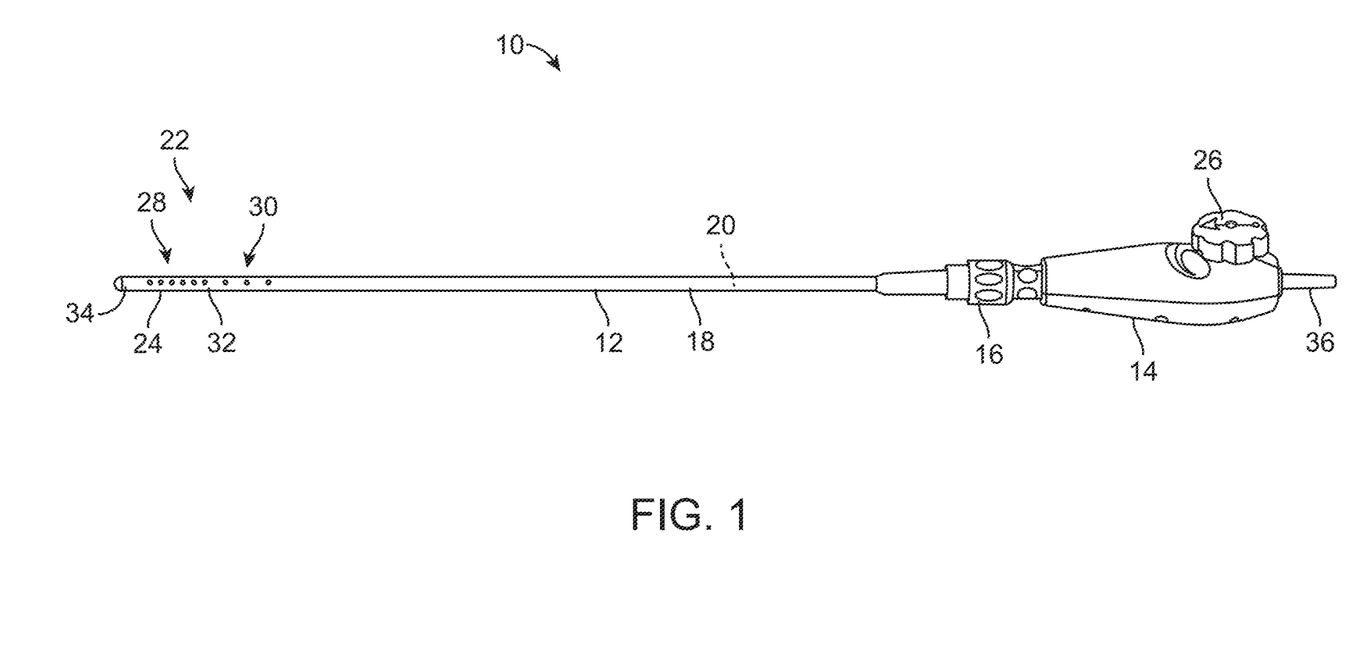
FIG. 1 shows a side view of one variation of an endoscopic device which provides for electromagnetic tracking as well as deflection of esophageal tissue when actuated.

One example of an instrument 10 which may incorporate such a sensor is shown in the side view of FIG. 1 which illustrates an endoscopic instrument 10 having an elongate body 12 which is advanceable into the patient body perorally through the mouth and at least partially into the esophagus. The elongate body 12 may have a length which ranges from, e.g., 15 to 75 cm, extending from a handle assembly 14 which may remain outside the patient body. The handle assembly 14 may incorporate an actuator such as a knob or lever 26 which may be articulated by the user to reconfigure a distal portion 22 of the body 12 in a number of different configurations. The handle assembly 14 may also incorporate at least one port 36 through which a lumen may extend through the handle assembly 14 and through the body 12 to fluidly communicate with one or more openings 28, 30 defined along the distal portion 22.

The elongate body 12 may be further comprised of a sheath 18 which extends over an underlying structure 20 attached to the handle assembly 14 and which provides structural support to the body 12 such that the body 12 may be advanced into the and through the esophagus or other body lumen without buckling or kinking along its length. A proximal end of the sheath 18 may include a connector 16 for removable attachment to the handle assembly 14 so that the sheath 18 may be coupled and de-coupled from the handle. The distal portion of the sheath 18 may define the openings 28, 30 which allow for fluid communication between the internal lumen and the external surface of the sheath 18. The underlying structure may further incorporate a hinge or pivoting mechanism 32 which allows for the displacement or actuation of a distal member 24 relative to the remainder of the body 12. The distal member 24 may also incorporate a sensor 34 which allows for the detection of the instrument 10 when positioned within the body lumen.

Figure 2:
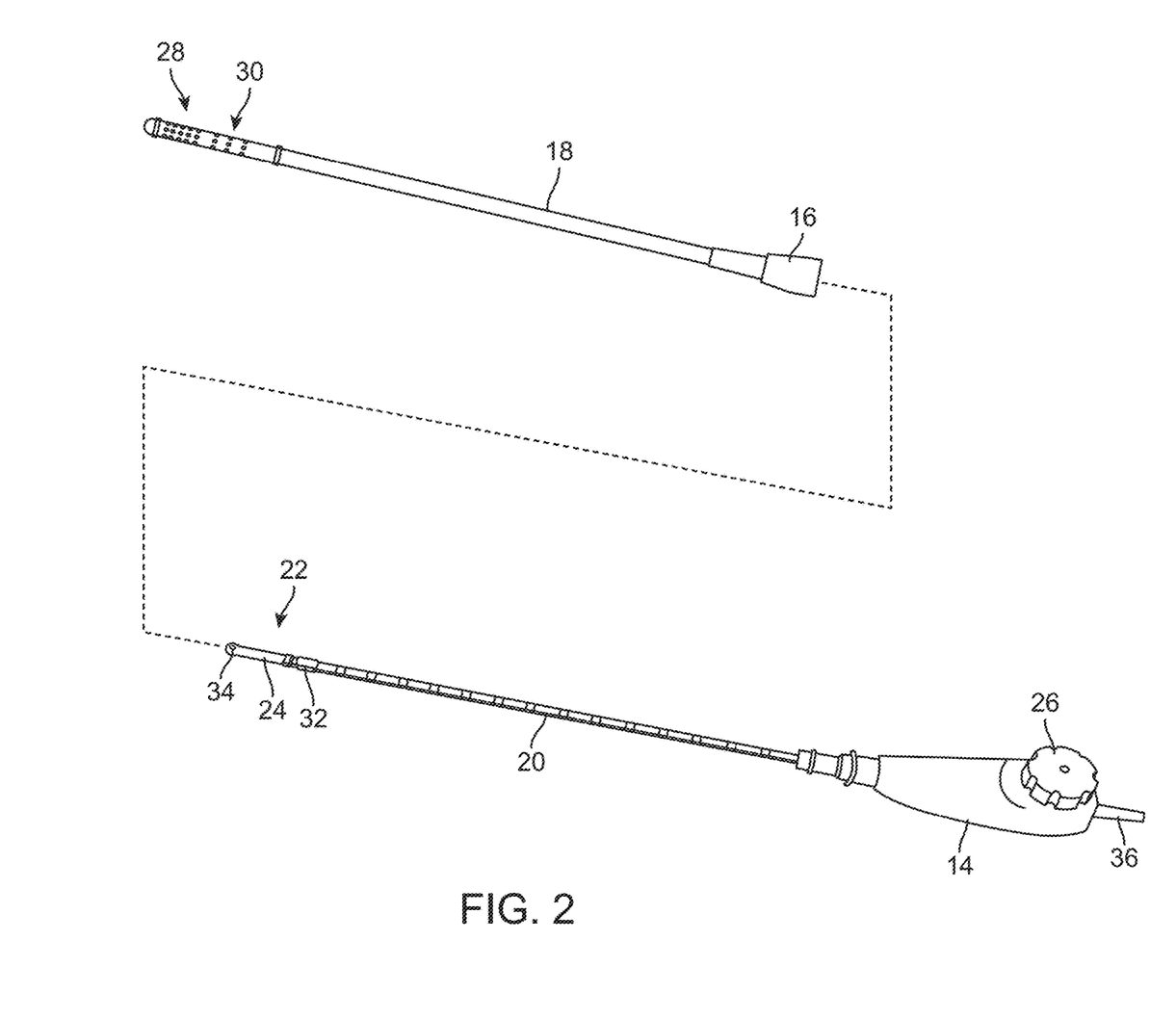
FIG. 2 shows a perspective assembly view of the endoscopic device with a sheath removed from the underlying elongate body.

FIG. 2 illustrates a perspective assembly view of the sheath 18 de-coupled from the handle assembly 14 and removed entirely from the underlying structure 20 for illustration purposes. The sheath 18 may be fabricated from any number of biocompatible materials which retain their flexibility such as silicone, polyvinylchloride (PVC), polyether- sulfone (PES), polyethylene (PE), polycarbonate (PC), polyetheretherketone (PEEK), polypropylene (PP), polysulfone (PS), polyurethane (PU), etc. Furthermore, while remaining coupled at its proximal end to the handle assembly 14 via the connector 16, the sheath 18 may remain unattached along its length to the underlying structure 20 or it may be coupled at one or more various points along its length, particularly along its distal portion.

The fluid port 36 is shown extending from the handle assembly 14 and one or more lumens may be defined along the length of the structure 20 to extend along its length and into fluid communication with the distal portion 22 of the structure 20 and body 12. A vacuum force may be drawn through the fluid port 36, e.g., via a pump (not shown), such that a negative fluid pressure is drawn through the distal portion 22 of the structure 20. This negative fluid pressure may draw any tissue in proximity or in contact against the outer surface of the openings 28, 30.

Figure 3A:
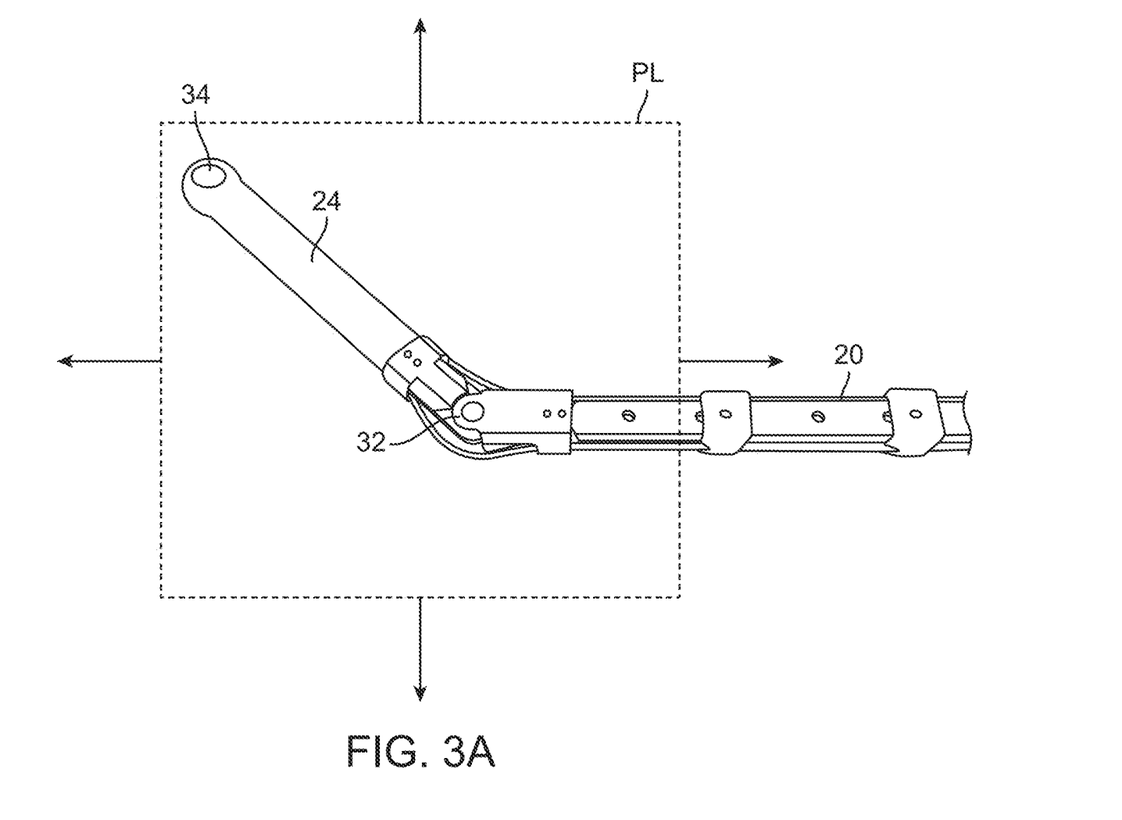
FIG. 3A shows a detail side view of a distal portion of the elongate body with the sheath removed to illustrate a deflection mechanism incorporating a pivoting structure.

FIG. 3A shows a side view of the distal portion 22 with the sheath 18 removed for illustrative purposes. The structure 20 may be comprised of a number of elongate plates or ribbon members which are layered to provide structural strength such that the structure 20 is relatively rigid within a rotational plane PL but which allows for some flexibility in the plane transverse to the rotational plane PL. The distal member 24 may be seen extending distally from the hinge or pivoting mechanism 32 and the sensor 34 may be seen positioned within or in proximity to the distal end of the device. The hinge or pivoting mechanism 32 may be configured to enable the distal member 24 to rotate about the hinge or pivoting mechanism 32 when the actuator 26 upon the handle assembly 14 is manipulated such that the distal member 24 rotates within the rotational plane PL. The rotation of the distal member 24 may be limited to rotate within a predetermined range within the plane PL, e.g., ±30 degrees, ±45 degrees, ±90 degrees, or any other angle lesser than or greater than 90 degrees, as practicable.

When the sheath 18 is positioned over the structure 20, the distal openings 28 along the sheath 18 may correspondingly be positioned along the distal member 24 distal to the hinge or pivoting mechanism 32 while the proximal openings 30 along the sheath 18 may correspondingly be positioned along the structure 18 proximal to the hinge or pivoting mechanism 32. The distal openings 28 may be positioned in a pattern which is relatively more dense than a pattern of the proximal openings 30 such that the tissue in proximity to the distal openings 28 may be more securely adhered to the distal openings 24 when a suction force is drawn through the openings 28, 30.

Figure 3B:
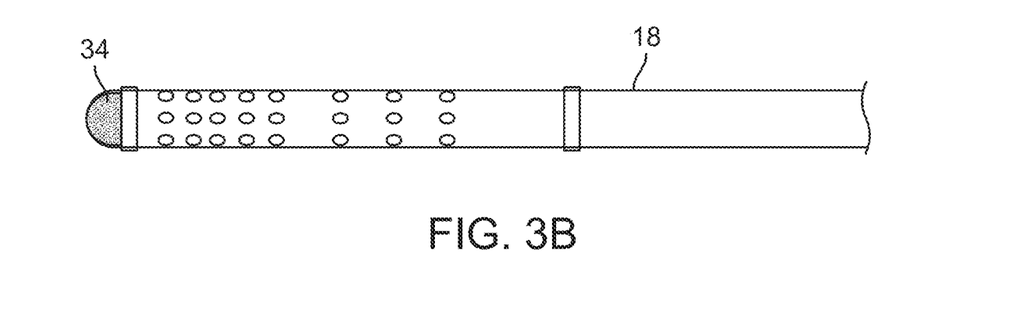
FIG. 3B shows a detail side view of a distal portion of the sheath to illustrate an alternative location for positioning of the sensor.

Another variation is shown in the detail side view of FIG. 3B where the sensor 34 may be positioned within the sheath 18 itself rather than along the distal member 24. In this variation, the sensor 34 may be located along the sheath 18 such as the distal tip with one or more lumens defined through the length of the sheath 18 for connection to the sensor 34. Optionally, lumens through the sheath 18 may also be provided for fluidly coupling to the fluid openings defined along the sheath 18.

It is intended that the instrument 10 may incorporate any of the different embodiments described herein in various combinations. For example, the instrument 10 may incorporate a sheath 18 having the sensor located along the distal member 24 or along the sheath 18 itself. Additionally, such a combination may incorporate lumens along the structure or along the sheath 18 or both. These examples are not intended to be limiting of the various possible combinations.

Turning now the sensor 34 positioned near or at the distal end of the elongate body 12, the instrument 10 may incorporate at least a single sensor 34 although any number of additional sensors may be incorporated along the body 12. A second instrument, e.g., ablation catheter, which may be used in a corresponding manner with the instrument 10 may also incorporate at least a single sensor near or at its distal tip, as described in further detail below. Any number of additional instruments may also be used in combination with instrument 10 and each additional instrument may incorporate at least a single sensor as well to be used in a corresponding manner with the instrument 10.

Figure 4A:
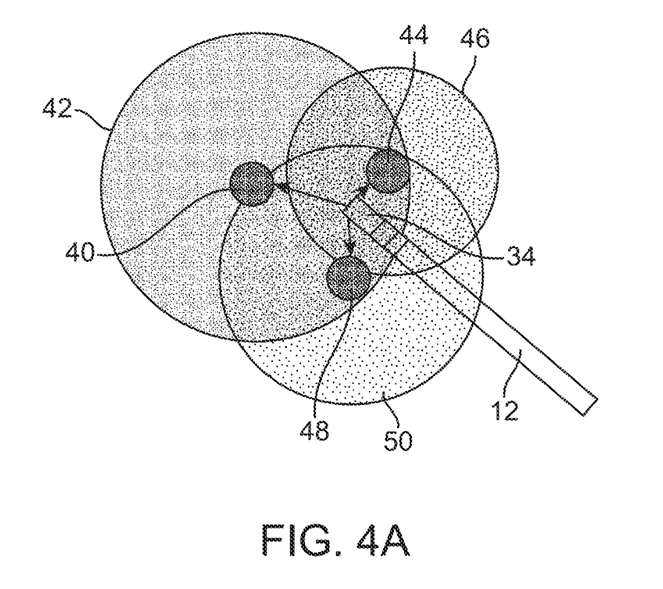
FIGS. 4A and 4B show schematic views of one variation of how the electromagnetic sensor within the device may be used for positional tracking.
Figure 4B:
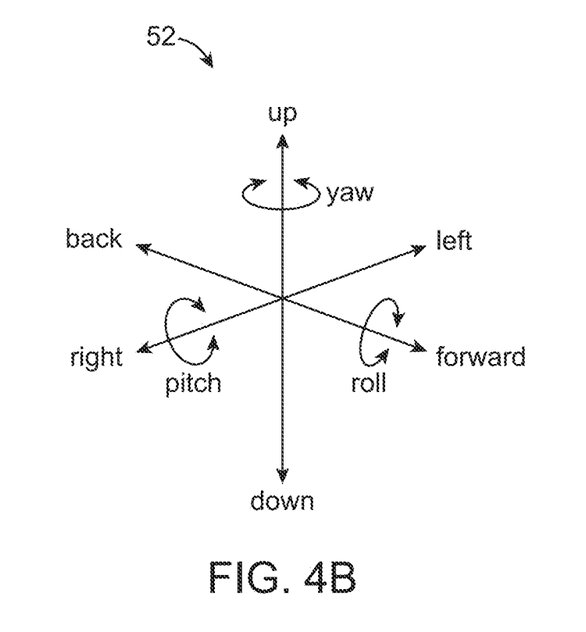

Regardless of the number of additional instruments utilized, the instrument 10 may utilize the sensor 34 near or at the tip of the instrument 10 which may be detected by the navigational system positioned externally of the patient body. The navigational system may generally incorporate multiple coils in proximity to or in contact with the external surface of the patient body. In one variation, as shown schematically in FIG. 4A, the system may use a first coil 40 which emits a first electromagnetic field 42, a second coil 44 positioned at a distance from the first coil 40 and which emits a second electromagnetic field 46, and a third coil 48 positioned at a distance from the first coil 40 and the second coil 44 and which emits a third electromagnetic filed 50. Each of the coils 40, 44, 48 may be used to detect not only the sensor 34 in the instrument 10 but also any other sensors in other instruments used in combination with the instrument 10. FIG. 4B illustrates an example of how the navigational system may be used to detect the position of the sensor 34 and hence the instrument 10 in space relative to the coils 40, 44, 48 as well as relative motion of the instrument 10 (e.g., up-down, back-forward, left-right, roll, yaw, pitch) in space as illustrated by schematic 52.

Figure 4C:
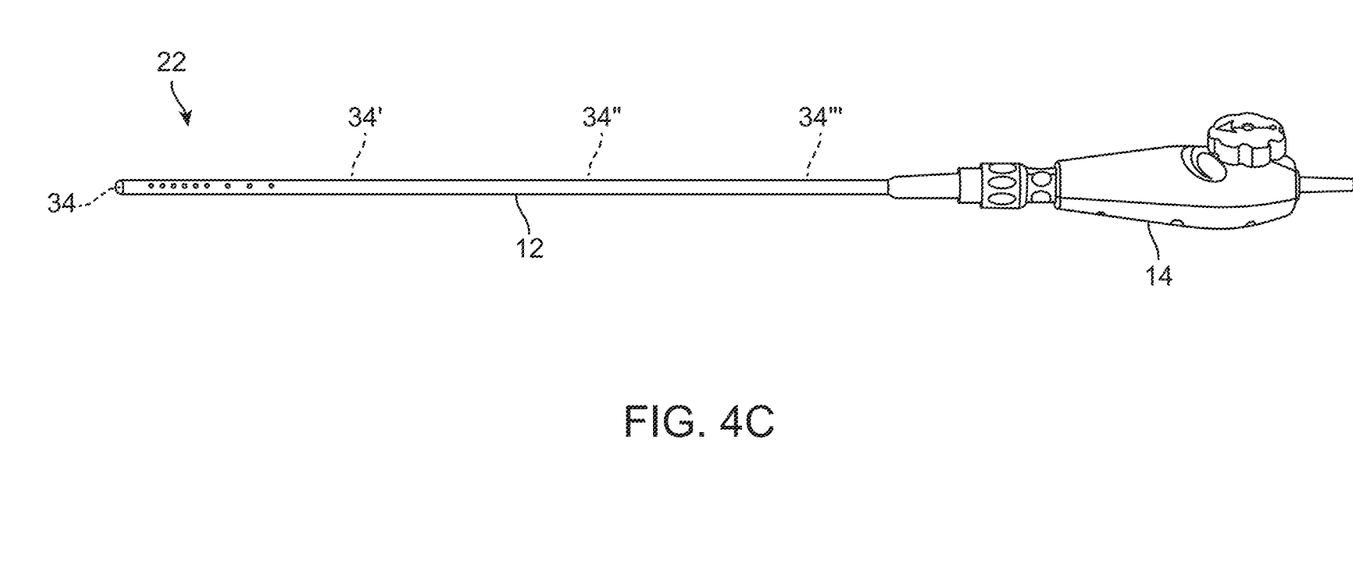
FIG. 4C shows a side view of another variation of the endoscopic device having multiple positioning sensors incorporated.
Figure 5A:
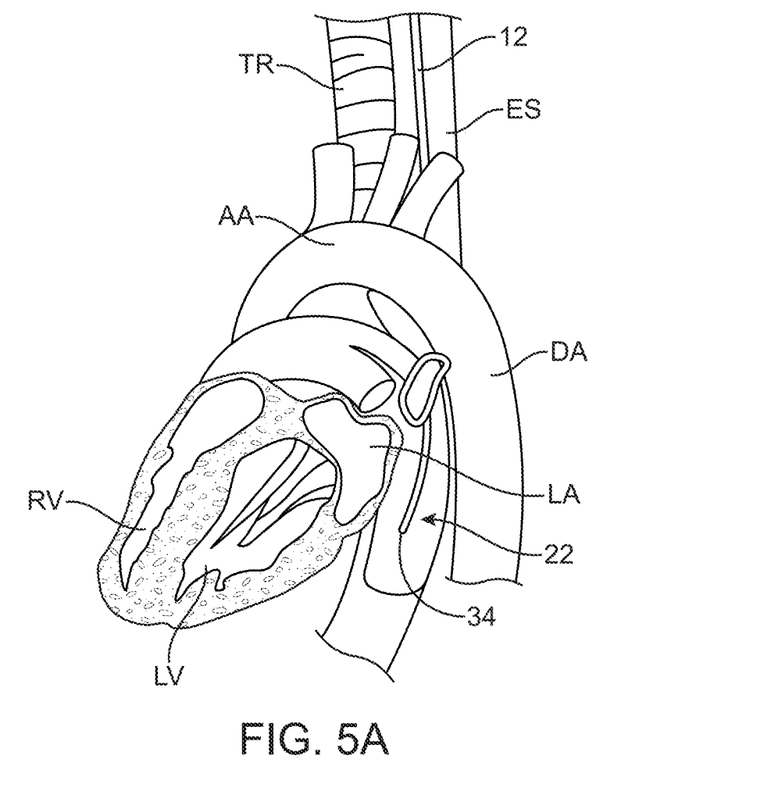
FIG. 5A shows a partial cross-sectional side view of a heart and esophagus to illustrate their relative positioning within the patient body.
Figure 5B:
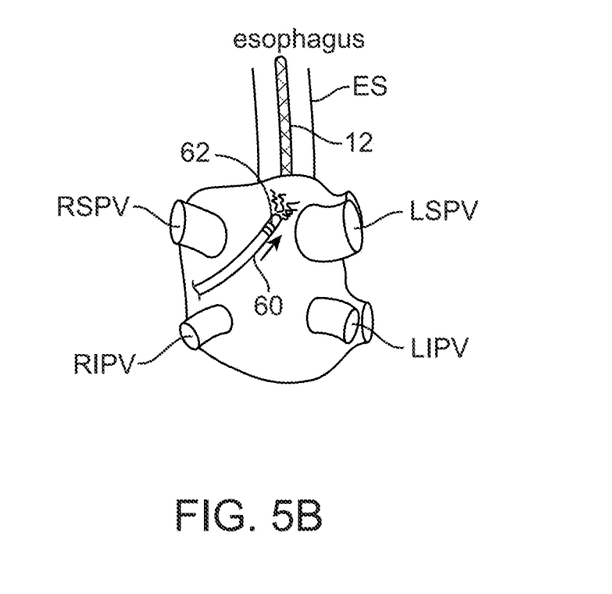
FIG. 5B shows a partial front view from within the left atrium of a heart to illustrate the relative positioning of the esophageal device positioned within the esophagus and in proximity to the heart and an ablation catheter positioned within the left atrium or other regions of the heart or vascular system for an ablation procedure.

With the instrument 10 inserted into and positioned within the esophagus of the patient, a single sensor 34 at the distal tip may be used. Although in other variations, as shown in FIG. 4C, the elongate body 12 may incorporate multiple sensors 34', 34", 34''' along the body 12. A fewer number or greater number of sensors may be used depending upon the desired application. With the use of multiple sensors, the elongate body 12 may be used to assess the positional relationship of the instrument 10 relative to the esophagus as well as the positional relationship of the ablation catheter relative to the instrument 10 and esophagus without require a constant movement of the instrument 10 within the esophagus as the ablation instrument is moved within the adjacent body lumen such as the heart or vascular system. This may also enable the system to determine the outer edges of the esophagus, e.g., to create a three-dimensional model of the esophagus. In this manner, the instrument 10 may be positioned once within the esophagus while the corresponding ablation catheter may be moved freely while the relative positioning can be tracked through the multiple sensors. FIG. 5A illustrates a partial cross-sectional side view (along a sagittal plane of the patient body) of the elongate body 12 advanced within the esophagus ES such that the sensor 34 and distal portion 22 are positioned within the esophagus ES at a location directly adjacent to where the left atrium LA of the heart or other regions of the heart or vascular system is in proximity or in direct contact against the exterior surface of the esophagus ES. The left ventricle LV and right ventricle RV of the heart are indicated for reference as well as the aortic arch AA, descending aorta DA, and trachea TR of the patient body. FIG. 5B illustrates a partial cross-sectional view from within the patient heart (along a coronal plane of the patient body) of the second instrument such as an ablation catheter 60 having a location sensor 62 positioned along the ablation catheter 60 near or at the distal tip. The ablation catheter 60 may be seen as having been advanced intravascularly into the left atrium LA of the heart (or can be positioned in other chambers of the heart or in the vascular system), with the esophagus ES positioned posteriorly of the left atrium LA. The elongate body 12 of the instrument 10 is shown as having been positioned within the esophagus ES in proximity to the left atrium LA while the tip of the ablation catheter 60 is positioned in proximity to the ostia of the pulmonary veins/vascular system (LSPV, LIPV, RSPV, RIPV) for treatment such as tissue ablation.

Figure 5C:
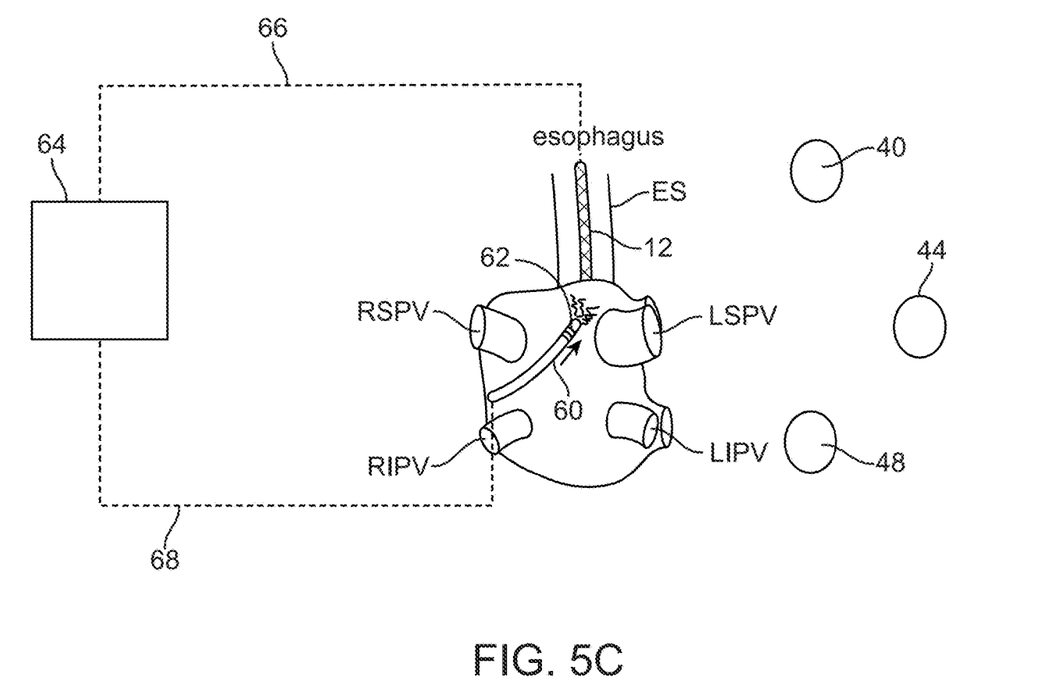
FIG. 5C shows an example of the esophageal device and ablation catheter in communication with a controller and with the navigational system.

FIG. 5C illustrates an example of how the one or more sensors, such as sensor 34, along the elongate body 12 may be in wired or wireless communication 66 with a controller 64 while the sensor 62 located along the ablation catheter 60 may also be in wired or wireless communication 68 with the controller 64. The detection coils 40, 44, 48 positioned in proximity to the patient body may be in communication with the controller 64 as well and used to determine the position of the elongate body 12 and ablation catheter 60 relative to one another. As the controller 64 may determine the relative distance between the distal portion 22 of the elongate body 12 and the ablation catheter 60, the controller 64 may also be programmed to provide an indication or alert to the user when the two instruments are within a predetermined distance from one another, e.g., 5 mm to 10 mm, or any selected distance as determined by the user. The distance determination may be performed with or without the use of another imaging modality such as fluoroscopy (which may be omitted altogether) during a treatment procedure.

Figure 6A:
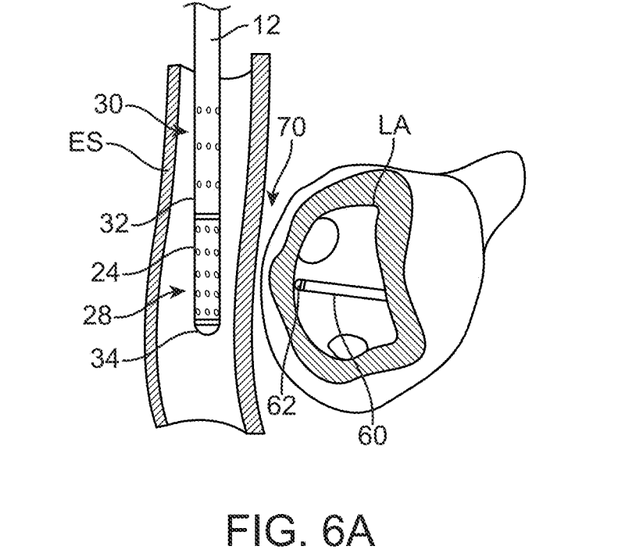
FIGS. 6A and 6B show an example of how the distal portion of the esophageal device may be actuated to defect the esophageal tissue away from the external surface of the heart or vascular system.
Figure 6B:
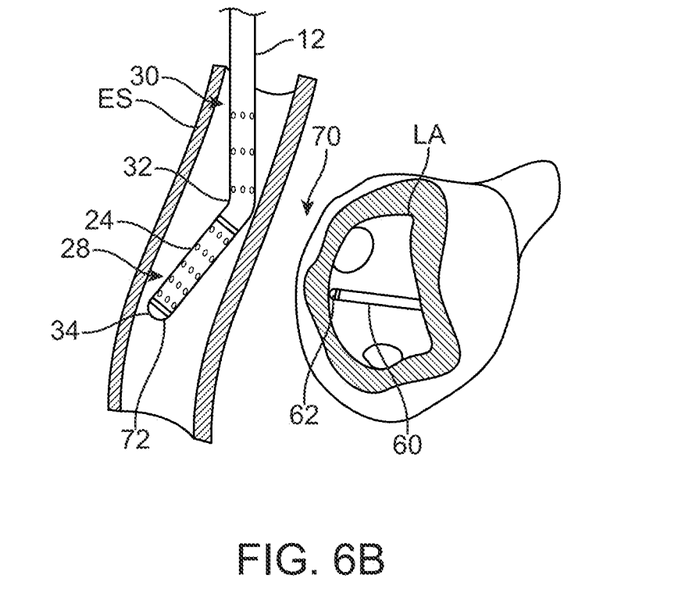

FIGS. 6A and 6B illustrate another example of how the instrument 10 may be used in an ablation procedure. FIG. 6A shows a partial cross-sectional side view (along a sagittal plane of the patient body) where the ablation catheter 60 has been intravascularly advanced into the left atrium LA (or other regions of the heart or vascular system) of the patient with the sensor 62 and ablation tip positioned in proximity or in contact against the interior of the left atrial tissue (or other regions of the heart or vascular system) for ablation treatment, e.g., for creating a conduction block. The elongate body 12 is shown as having been advanced per-orally into the esophagus ES such that the distal member 24 is positioned within the esophagus ES adjacent to the left atrium LA (or other regions of the heart or vascular system) of the patient. The suction force may be optionally actuated such that the esophageal tissue surrounding the distal and proximal openings 28, 30 may be adhered to the outer surface of the distal portion 24 of the elongate body 12.

The relative distance between the tip of the ablation catheter 60 and sensor 34 located on the elongate body 12 may be determined and monitored by the controller 64 prior to and/or during an ablation treatment. With a threshold distance between the ablation catheter and sensor 34 predetermined, e.g., 5 mm to 10 mm, or any selected distance as determined by the user, the ablation catheter 60 may be used to deliver ablation energy for tissue treatment. In the event that the ablation catheter 60 and sensor 34 are moved too close to one another within the threshold distance, an indication may be provided by the controller 64 to the user that the ablation catheter 60 may be too close to the esophageal tissue such that the ablation energy from within the left atrium LA, or other regions of the heart or vascular system, may be conducted through the tissue and inadvertently damage the adjacent esophageal tissue.

In the event that the ablation catheter 60 and esophageal tissue are determined to be too close to one another, the controller 64 may be programmed to provide the alert to the user and/or optionally automatically stop the ablation catheter 60 to prevent any esophageal tissue damage. The user may also actuate the knob or lever 26 on the handle assembly 14 to reconfigure the distal portion 24 to rotate within the plane PL relative to the remainder of the elongate body 12 in order to reposition a portion of the esophagus ES away from the exterior of the heart or vascular system such that a gap 70 is formed between the two, as shown in FIG. 6B. The distal portion 24 may be actuated while the surrounding esophageal tissue is adhered to the outer surface of the elongate body 12 via the suction force or with the suction force turned off although having the esophageal tissue adhered to the distal portion 24 when deflected can help ensure that the gap 70 is formed between the esophagus ES and heart tissue or vascular system.

While the distal portion 24 may be actuated manually by the user, the distal portion 24 in other variations may be actuated automatically by the controller 64 upon detecting that the ablation catheter 60 and elongate body 12 are too close to one another. In yet another variation, other sensors such as a temperature sensor 72 may be optionally incorporated along the elongate body 12 and used to monitor for a temperature rise due to the ablation energy from the ablation catheter 60. If the monitored temperature detected by the temperature sensor 72 rises above a predetermined threshold limit, the controller 64 may provide an indication or alert to the user. Additionally and/or alternatively, the controller 64 may also be programmed to either stop the ablation energy, actuate the distal portion 24 to deflect the esophageal tissue away, or both.

Another example of how the device may be used relates to treatments applied to a lung or lungs of the patient rather than the heart. Radiation energy may be applied to the lungs, for example, in treating tumors or lesions for lung cancer. The instrument 10 (or any of its variations described) may be positioned within the esophagus and used to deflect portions of the esophagus. By moving the esophagus out of the radiation port, collateral radiation damage to the esophagus may be reduced and may also allow for the delivery of a higher dose of radiation than would otherwise be possible if the esophageal tissue were present.

The applications of the disclosed invention discussed above are not limited to the embodiments described, but may include any number of other applications and uses. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of treating a tissue region within a heart or vascular system of a patient body, comprising:
    positioning an elongate body having a first sensor positioned near or at a distal end of a distal portion of the elongate body within an esophageal lumen in proximity to the heart of the patient body;
    positioning an ablation catheter having a second sensor positioned near or at a distal end of the ablation catheter within a left atrium or other regions of the heart or vascular system in proximity to the esophageal lumen;
    monitoring a distance between the first sensor within the esophageal lumen and the second sensor within the left atrium or other regions of the heart or vascular system;
    actuating the ablation catheter to deliver ablation energy to a tissue surface within the left atrium or other regions of the heart or vascular system while monitoring the distance; and
    actuating the elongate body to angularly rotate the distal portion about a pivoting mechanism to deflect a region of the esophageal lumen away from the left atrium or other regions of the heart or vascular system when the distance is below a threshold distance.

2. The method of claim 1 wherein positioning the elongate body comprises advancing the elongate body into the esophageal lumen.

3. The method of claim 1 wherein positioning the ablation catheter comprises intravascularly advancing the ablation catheter into the left atrium or other regions of the heart or vascular system.

4. The method of claim 1 wherein monitoring the distance comprises determining the distance via an electromagnetic navigational system in communication with the first sensor and the second sensor.

5. The method of claim 1 further comprising monitoring a temperature within the esophageal lumen via a temperature sensor.

6. The method of claim 1 wherein reconfiguring the distal portion further comprises drawing a suction force through the distal portion of the elongate body such that the region of the esophageal lumen is adhered to an outer surface of the distal portion of the elongate body.

7. The method of claim 1 wherein reconfiguring the distal portion comprises actuating a lever or knob on a handle assembly.

8. The method of claim 1 further comprising halting the ablation energy from the ablation catheter when the distance is below the threshold distance.

* * * * *